United States Patent
Irwin et al.

(10) Patent No.: US 11,395,615 B2
(45) Date of Patent: Jul. 26, 2022

(54) FATIGUE AND DROWSINESS DETECTION

(71) Applicant: BOSE CORPORATION, Framingham, MA (US)

(72) Inventors: Alexander Irwin, Belmont, MA (US); Ankita Singh, Hudson, MA (US)

(73) Assignee: BOSE CORPORATION, Framingham, MA (US)

( * ) Notice: Subject to any disclaimer, the term of this patent is extended or adjusted under 35 U.S.C. 154(b) by 500 days.

(21) Appl. No.: 16/386,916

(22) Filed: Apr. 17, 2019

(65) Prior Publication Data
US 2020/0330017 A1    Oct. 22, 2020

(51) Int. Cl.
| A61B 5/256 | (2021.01) |
| A61B 5/16 | (2006.01) |
| A61B 5/00 | (2006.01) |
| A61B 5/024 | (2006.01) |
| A61B 5/25 | (2021.01) |
| A61B 5/296 | (2021.01) |
| A61B 5/398 | (2021.01) |

(52) U.S. Cl.
CPC .......... *A61B 5/163* (2017.08); *A61B 5/02405* (2013.01); *A61B 5/165* (2013.01); *A61B 5/25* (2021.01); *A61B 5/296* (2021.01); *A61B 5/398* (2021.01); *A61B 5/6803* (2013.01)

(58) Field of Classification Search
CPC .......... A61B 5/16; A61B 5/162; A61B 5/163; A61B 5/165; A61B 5/168; A61B 5/18; A61B 5/25; A61B 5/251; A61B 5/256; A61B 5/28; A61B 5/291; A61B 5/296; A61B 5/297; A61B 5/389; A61B 5/397; A61B 5/68; A61B 5/6802; A61B 5/6803
USPC .................................. 600/301, 509, 546
See application file for complete search history.

(56) References Cited

U.S. PATENT DOCUMENTS

| 9,579,060 B1 * | 2/2017 | Lisy .................... A61B 5/6803 |
| 2005/0004489 A1 * | 1/2005 | Sarkela ................ A61B 5/4821 600/383 |
| 2007/0060830 A1 * | 3/2007 | Le ........................ A61B 5/165 600/546 |

(Continued)

FOREIGN PATENT DOCUMENTS

GB    2396421 A *  6/2004  .......... A61B 5/6803

OTHER PUBLICATIONS

Schleicher, et al., "Blinks and Saccades as Indicators of Fatigue in Sleepiness Warnings: Looking Tired?", Ergonomics, vol. 51, No. 7, Jul. 2008, 982-1010.

*Primary Examiner* — Ahmed M Farah
(74) *Attorney, Agent, or Firm* — Patterson + Sheridan, LLP

(57) ABSTRACT

Aspects provide a system including a wearable audio device. The system is configured to determine one or more states of a subject using electrodes positioned on the wearable audio device and in contact with the subject's body. Three electrodes on the wearable audio device are configured to collect any combination of EMG, EOG, ECG/EKG. The system is configured to determine if the subject is fatigued, attentive, anxious, or stressed. The system determines the subject's state without use of a camera. In addition to determining one or more states of the subject, the subject can control the audio device based on a pattern of pupil movements. According to aspects, eye location determined using collected signals are used to adjust and enhance an output of an augmented reality application.

11 Claims, 10 Drawing Sheets

(56) References Cited

U.S. PATENT DOCUMENTS

| | | | | |
|---|---|---|---|---|
| 2007/0276281 A1* | 11/2007 | Sarkela | ................... | A61B 5/24 |
| | | | | 600/546 |
| 2013/0011819 A1* | 1/2013 | Horseman | ............ | A61B 5/0537 |
| | | | | 434/257 |
| 2015/0354941 A1* | 12/2015 | Heaton | ................ | A61N 1/0452 |
| | | | | 607/48 |
| 2018/0161579 A1* | 6/2018 | Franke | ................... | A61B 5/389 |
| 2020/0390997 A1* | 12/2020 | Jovanov | ................ | A61M 21/00 |
| 2021/0169417 A1* | 6/2021 | Burton | ............... | A61B 5/02055 |

* cited by examiner

FATIGUE AND DROWSINESS DETECTION

FIELD

Aspects of the disclosure relate to detecting fatigue and drowsiness using electrodes on a wearable consumer product. In addition to detecting fatigue and drowsiness, the wearable products described herein are further configured to detect any combination of a user's level of attentiveness, gaze direction, heart rate, heart rate variability, and level of stress.

BACKGROUND

Monitoring a subject's level of fatigue is a significant consideration in certain fields including the aviation, automotive, and military settings. Subjects may work long shifts and perform repetitive or monotonous tasks. Conventional approaches for monitoring a subject's level of fatigue rely on a camera to continuously track eyes under field conditions. Aside from low sampling rate, tracking the eyes continuously under field conditions is challenging for camera systems. Additionally, it is challenging for camera systems to distinguish between overlong eyelid closures and facial expressions or head turns where the subject's eyes are not trackable. There is a need for improving the methods for detecting fatigue as well as other physiological conditions.

SUMMARY

All examples and features mentioned herein can be combined in any technically possible manner.

Aspects provide a system comprising a first, second, and third electrode on a wearable audio device and a processor. The first electrode is positioned on a first side of the wearable audio device, the second electrode is positioned on a second side of the wearable audio device, and the third electrode on positioned anyplace on the wearable audio device. The processor is in communication with the wearable audio device and configured to: determine an electromyogram based on signals collected from the first, second, and third electrodes, determine a frequency of eye blinking associated with a subject wearing the wearable audio device based on the electromyogram, determine a duration of eye blinking associated with the subject based on the electromyogram, and determine a level of fatigue of the subject based on the frequency and the duration of eye blinking.

In an aspect, the processor is further configured to: determine an electrooculogram based on the signals collected from the first, second, and third electrodes, determine pupil movement of the subject based on the electrooculogram, wherein the pupil movement comprises at least one of a pupil moving from left to right or the pupil moving from right to left, and determine a level of attentiveness of the subject based on the pupil movement. In an aspect, the processor is further configured to determine a direction of gaze of the subject based on the pupil movement.

In an aspect, the processor is further configured to: determine an electrocardiogram based on the signals collected from the first, second, and third electrodes, determine a heart rate or heart rate variability based on the electrocardiogram, and determine a level of stress of the subject based on the heart rate or heart rate variability.

In an aspect, the first electrode is positioned over the right temporalis of the subject, and the second electrode is positioned over the left temporalis of the subject. In an aspect, the third electrode is positioned over one of the: frontal belly of occipitofrontalis of the subject, corrugator supercilli of the subject, or procerus of the subject.

In an aspect, the wearable audio device comprises an aviation headset. In an aspect, the wearable audio device comprises audio eyeglasses. In an aspect, the processor is external to the wearable audio device.

Certain aspects provide a system comprising a first, second, and third electrode and a processor. The first electrode is positioned on a first side of audio eyeglasses, the second electrode is positioned on a second side of the audio eyeglasses, and the third electrode is positioned on the audio eyeglasses. The processor is in communication with the audio eyeglasses and configured to: determine an electromyogram based on signals collected from the first, second, and third electrodes, determine a frequency of eye blinking associated with a subject wearing the audio eyeglasses based on the electromyogram, determine a duration of eye blinking associated with the subject based on the electromyogram, and determine a level of fatigue of the subject based on the frequency and the duration of eye blinking.

In aspects, the first electrode is positioned over the right temporalis of the subject, the second electrode is positioned over the left temporalis of the subject, and the third electrode is positioned over the procerus of the subject.

In aspects, the first electrode positioned over the right temporalis is disposed on the right arm of the audio eyeglasses and the second electrode positioned over the left temporalis is disposed on the left arm of the audio eyeglasses.

In aspects, the processor is further configured to determine an electrooculogram based on the signals collected from the first, second, and third electrodes and determine pupil movement of the subject based on the electrooculogram, wherein the pupil movement comprises at least one of a pupil moving from left to right or the pupil moving from right to left. In aspects, the processor is further configured to determine a level of attentiveness of the subject based on the pupil movement. In aspects, the processor is further configured to determine a direction of gaze of the subject based on the pupil movement. In aspects, the processor is further configured to control the audio eyeglasses based on the pupil movement.

In aspects, the processor is further configured to determine a location of at least one pupil of the subject based on the signals collected from the first, second, and third electrodes and enhance an augmented reality output by the audio eyeglasses based, at least in part, on the location of the at least one pupil.

In aspects, the processor is further configured to: determine an electrocardiogram based on the signals collected from the first, second, and third electrodes, determine a heart rate or heart rate variability based on the electrocardiogram, and determine a level of stress of the subject based on the heart rate or heart rate variability.

In aspects, the processor is further configured to control the audio eyeglasses based on at least one of: the frequency and duration of eye blinking.

Certain aspects provide a system comprising a first electrode on a wearable audio device positioned on a first side of the wearable audio device, a second electrode on the wearable audio device positioned on a second side of the wearable audio device, and a third electrode on the wearable audio device, and a processor in communication with the wearable audio device. The processor is configured to: determine at least one of: an electromyogram, an electrooculogram, and an electrocardiogram based on signals collected from the first, second, and third electrodes, determine a frequency of eye blinking associated with a subject wearing the wearable audio device based on the electromyogram, determine a duration of eye blinking associated with the subject based on the electromyogram, and determine a level of fatigue of the subject based on the frequency of eye blinking.

In aspects, the processor is further configured to determine pupil movement of the subject based on the electrooculogram, wherein the pupil movement comprises at least one of a pupil moving from left to right or the pupil moving from right to left and determine a level of attentiveness of the subject based on the pupil movement. In aspects, the processor is further configured to control the wearable audio device based on the pupil movement.

In aspects, the processor is further configured to determine a location of at least one pupil based on the signals collected from the first, second, and third electrodes and enhance an augmented reality output by the wearable audio device based, at least in part, on the location of the at least one pupil.

In aspects, the processor is further configured to determine a heart rate or heart rate variability based on the electrocardiogram and determine a level of stress of the subject based on the heart rate or heart rate variability.

In aspects, the first electrode is positioned over the right temporalis of the subject, the second electrode is positioned over the left temporalis of the subject, and the third electrode is positioned over one of: the corrugator supercilii of the subject or the procerus of the subject.

Two or more features described in this disclosure, including those described in this summary section, can be combined to form implementations not specifically described herein. The details of one or more aspects are set forth in the accompanying drawings and the description below. Other features, objects, and advantages will be apparent from the description, drawings, and the claims.

DETAILED DESCRIPTION

Figure 1A:
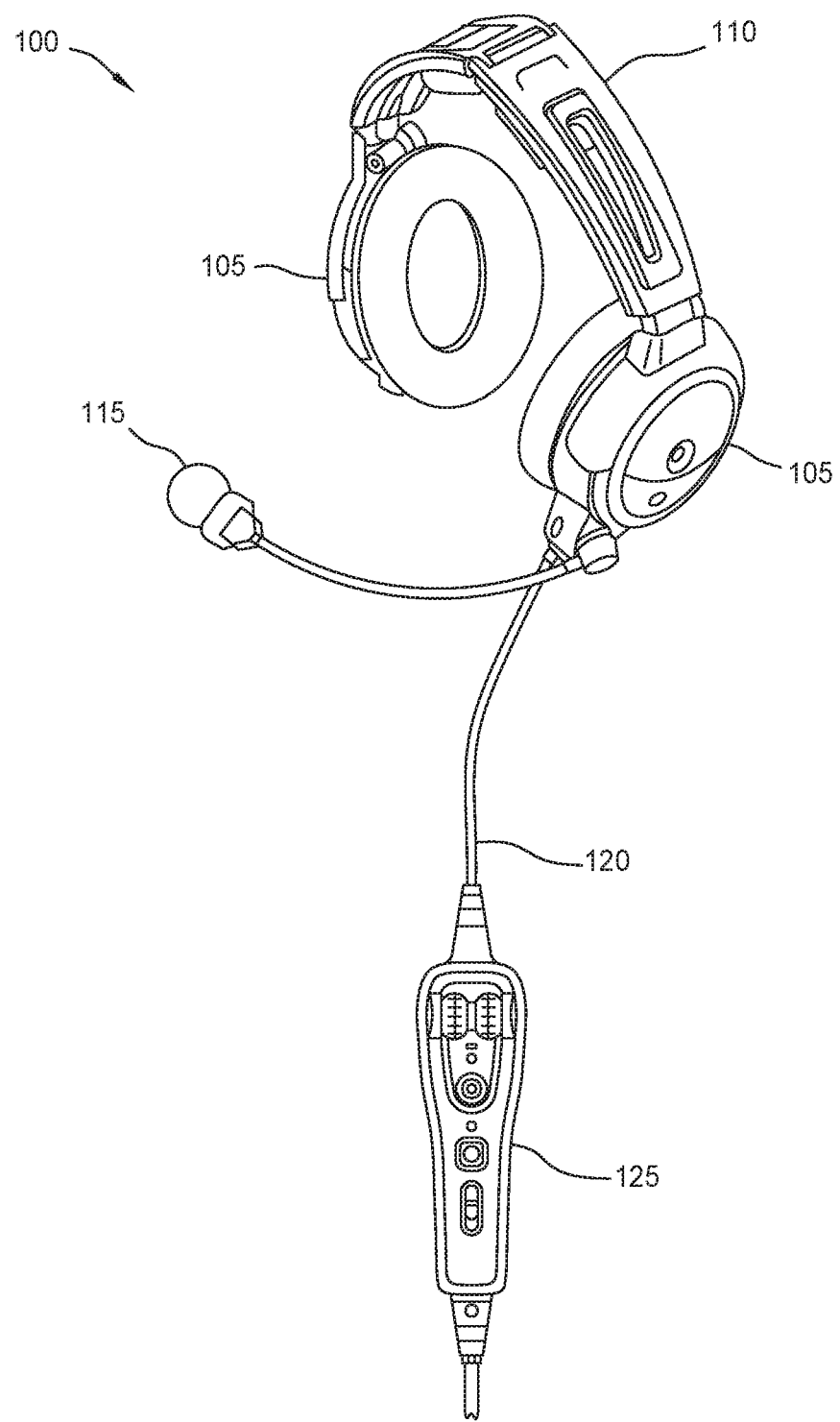
FIG. 1A illustrates an example of an aviation headset.

Studies show a correlation between eye blink behavior and a subject's level of fatigue. Blink frequency and blink duration are two indicators of a subject's level of fatigue. See e.g., R. Schleicher, N. Galley, S. Briest & L. Galley (2008) Blinks and saccades as indicators of fatigue in sleepiness warnings: looking tired?, Ergonomics, 51:7, 982-1010, DOI:10.1080/00140130701817062.

Aspects of the present disclosure describe techniques for detecting fatigue by a wearable audio device. For purposes of this description, fatigue, drowsiness, and tiredness may be used interchangeably. In an example, fatigue is characterized by a lack of energy. As a subject's level of fatigue increases, his or her frequency of blinking and duration of each blink both increase. Aspects further describe techniques for detecting other states, characteristics, or biologically-relevant parameters including a level of attentiveness or focus, a direction of gaze, a heart rate (HR), or heart rate variability (HRV).

In contrast to conventional approaches, various implementations include devices, systems, and related methods for detecting fatigue and other states and characteristics based on signals collected from electrodes placed on the wearable audio device and in contact with the subject's body. Advantageously, the implementations described herein do not use a camera to monitor the subject's blinking or eye movements to determine a state of a subject. As described herein, a wearable audio device is configured to collect information in real-time to determine a state of the subject and take action based on the determined state. The determined state of the subject can be used, alone or in combination with other data, to alert the subject that he or she is fatigued or introduce an intervention when the subject is fatigued. The other data is associated with any combination of physiological factors associated with the subject or external factors. Examples of external factors include, for example, the weather conditions, how long the subject has been working over a period of time, level of experience of the subject, or subject-specific abnormalities determined using any combination of subject input and machine learning.

Wearable audio devices are used for work and pleasure. A wearable audio device may include aviation, military, or automotive headsets, over-the-ear headphones, audio eyeglasses or frames, military eyeglasses, in-ear headphones or earbuds, around-ear devices, on-neck devices, open-ear audio devices (e.g., a wearable audio device that includes an acoustic driver to radiate acoustic energy towards the ear while leaving the ear open to its environment and surroundings), or other wearable audio devices such as smart watches, headbands or the like. In some aspects, a wearable audio device is configured to be worn in or on at least a portion of a subject's head and/or on at least a portion of a subject's neck. In an aspect, a wearable audio device includes one or more microphones to detect sound in the vicinity of the wearable audio device. In aspects, the wearable audio device also includes at least one acoustic transducer (also known as driver or speaker) for outputting sound. The included acoustic transducer is configured to transmit audio through air and/or through bone (e.g., via bone conduction, such as through the bones of the skull).

In an aspect, a wearable audio device includes hardware devices and circuitry to implement one or more of noise cancelling, sound masking, movement detection, voice activity control, and geolocation determination. Noise canceling circuitry is configured to reduce sounds external to the wearable audio device by using active noise canceling. The sound masking circuitry is configured to reduce or "mask" distractions by outputting masking sounds using the speakers of the wearable audio device. In an example, the movement detection is performed using one or more of an accelerometer, gyroscope, or magnetometer to detect whether the subject is moving and/or the direction the subject is looking or facing. In aspects, movement detecting circuitry is configured to detect a head position of the subject for use in augmented reality (AR) applications where an AR sound is played back based on the direction the user is facing. In an aspect, voice activity control detects the presence of human speech signals in a sound signal received by the microphones in the wearable audio device. In an aspect, the geolocation circuitry includes a Global Positioning System (GPS) antenna and related circuitry to determine a physical location (GPS coordinates) of the subject.

According to an aspect, a wearable audio device is communicatively coupled with a portable user device smart phone or computing tablet. In an aspect, the wearable audio device is wirelessly connected to the portable user device using one or more wireless communication methods including but not limited to Bluetooth, Wi-Fi, Bluetooth Low Energy (BLE), or other radio frequency (RF)-based techniques. In an aspect, the wearable audio device is connected to the portable user device using a wired connection, with or without a corresponding wireless connection. In an aspect, the wearable audio device is connected to a network (e.g., the Internet) and can access one or more cloud services over the network. In aspects, the user device is connected to a network, and the wearable audio device connects to the network to access one or more services using the user device. In an aspect, the wearable audio device includes a transceiver that transmits and receives information via one or more antennae to exchange information with the user device or network. In an aspect, the wearable audio device includes one or more electrodes positioned to collect electrical signals from the subject to determine if a subject is fatigued and, optionally, other states of the subject.

In aspects, the wearable audio device includes hardware and circuitry including processor(s)/processing system and memory configured to implement detecting when a subject is fatigued and other states described herein.

In aspects, the wearable audio device includes hardware and circuitry including processor(s)/processing system and memory configured to implement determining an electromyogram (EMG) based on signals collected from electrodes positioned on the wearable audio device. In an example, an EMG may be determined based on signals collected from one or more electrodes positioned over the frontal belly of occipitofrontalis, over the corrugator supercilii, over the procerus, over the right temporalis, and/or over the left temporalis. The EMG may be used to determine a frequency and/or duration of eye blinking associated with the subject, which in turn may be used to determine a level of fatigue of the subject based on the frequency of eye blinking.

In aspects, the wearable audio device includes hardware and circuitry including processor(s)/processing system and memory configured to implement determining an EMG based on: signals collected from an electrode positioned over the procerus, an electrode positioned over the right temporalis, and an electrode positioned over the left temporalis, determining a frequency and/or duration of eye blinking associated with the subject based on the EMG, and determining a level of fatigue of the subject based on the frequency of eye blinking.

In aspects, the wearable audio device includes hardware and circuitry including processor(s)/processing system and memory configured to implement determining an EMG based on: signals collected from an electrode positioned over the corrugator supercilii, an electrode positioned over the right temporalis, and an electrode positioned over the left temporalis, determining a frequency and/or duration of eye blinking associated with the subject based on the EMG, and determining a level of fatigue of the subject based on the frequency of eye blinking.

In aspects, the wearable audio device includes hardware and circuitry including processor(s)/processing system and memory configured to implement determining an EMG based on: signals collected from an electrode positioned over the frontal belly of occipitofrontalis, an electrode positioned over the right temporalis, and an electrode positioned over the left temporalis, determining a frequency and/or duration of eye blinking associated with the subject based on the EMG, and determining a level of fatigue of the subject based on the frequency of eye blinking.

In aspects, the wearable audio device includes hardware and circuitry including processor(s)/processing system and memory configured to implement determining an electrooculogram (EOG) based on: signals collected from an electrode positioned over the left temporalis, the right temporalis, and a third electrode, determining pupil eye movement associated with the subject based on the EOG, and determining a level of attentiveness of the subject based on the pupil movement. Pupil movement determined from an EOG refers to at least one of the pupil moving from the left side of the subject's eye to the right side of the subject's side or the pupil moving from the right side of the subject's eye to the left side of the subject's eye.

In aspects, the wearable audio device includes hardware and circuitry including processor(s)/processing system and memory configured to implement determining an electrocardiogram (ECG or EKG) based on: signals collected from an electrode positioned over the left temporalis, the right temporalis, and a third electrode, determining a HR or HRV associated with the subject based on the ECG/EKG, and determining a level of stress of the subject based on the HR or HRV.

While specific form factors and electrode placements on the form factions are described herein for illustrative purposes, generally three electrodes positioned on the wearable audio device are used to estimate any combination of the subject's EMG, EKG/ECG, and EOG. One of the three electrodes is a reference electrode. The reference electrode, and a voltage potential between the other two electrodes are used to determine the EMG, EKG/ECG, and/or EOG. In an aspect, the reference electrode is positioned any place on the wearable audio device. Regarding the other two electrodes, in an aspect, one electrode is placed on each side of the subject's body. In another aspect, both of the electrodes are positioned on the same side of the subject. In aspects, the active and reference electrodes change based on the measurement taken. Regardless of where the three electrodes are placed on the wearable audio device, the same three electrodes are used to estimate any combination of the subject's EMG, ECG/EKG, and/or EOG.

Figure 1B:
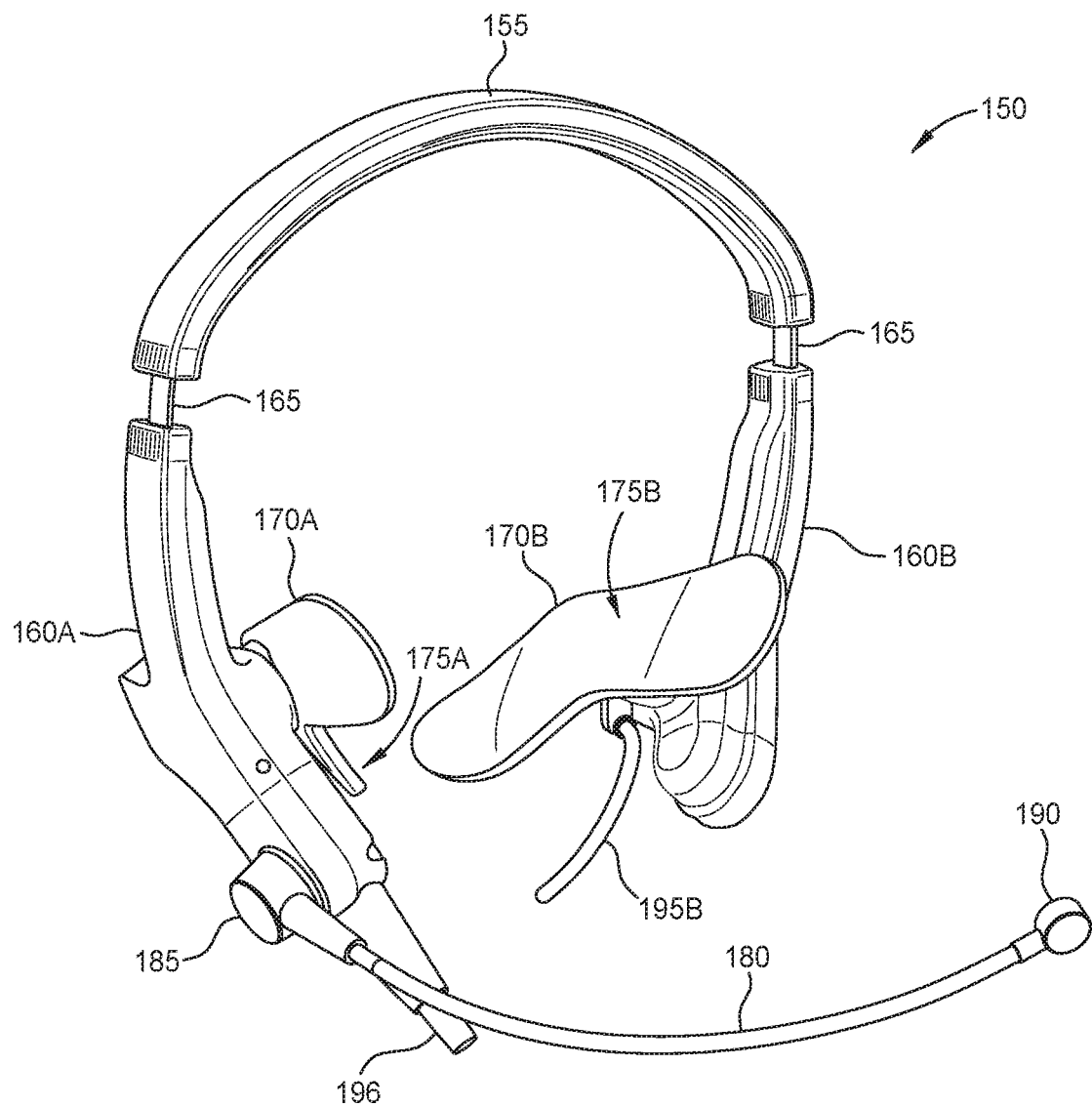
FIG. 1B illustrates an example of an aviation headset.
Figure 2:
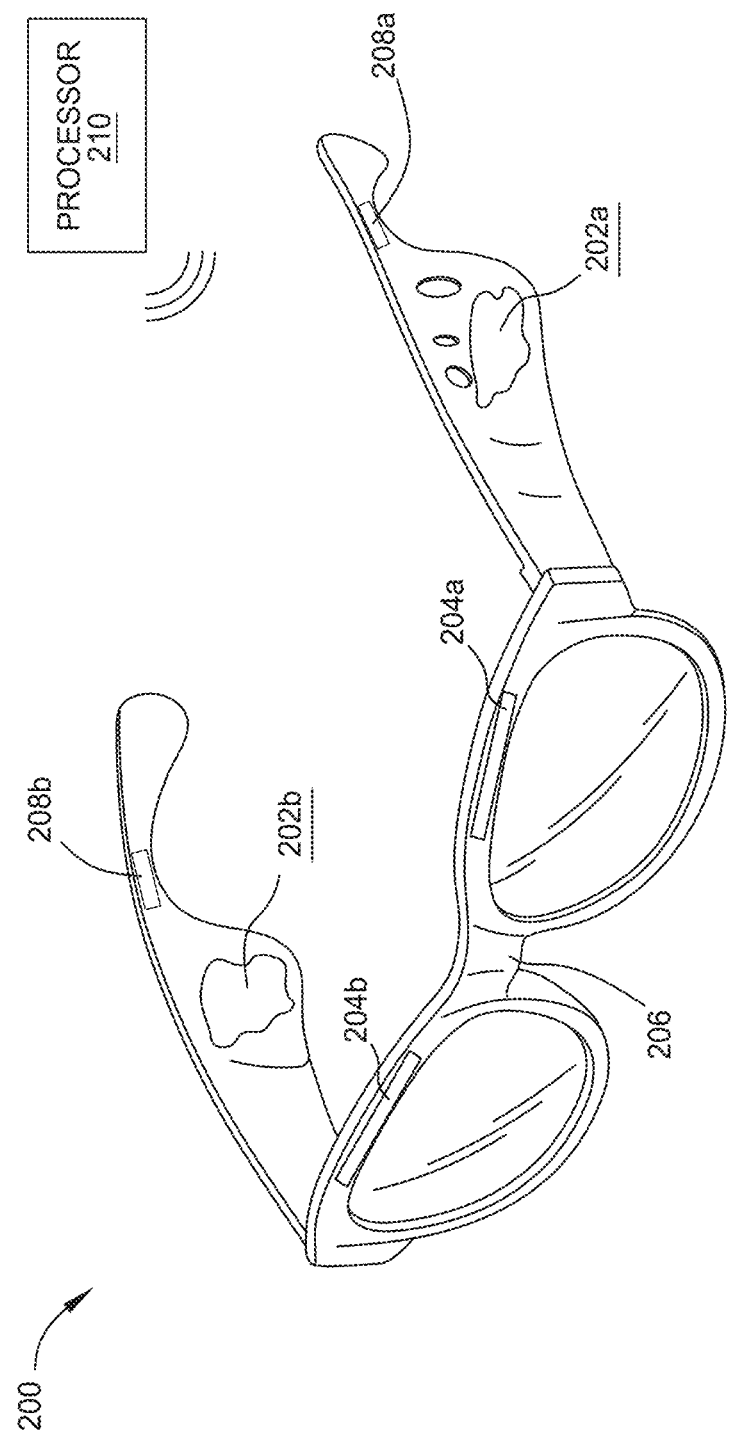
FIG. 2 illustrates an example of audio eyeglasses.

FIGS. 1A, 1B, and 2 illustrate example form factors of a wearable audio device; however, the systems and methods for detecting fatigue, alertness, direction of gaze, HR, HRV, stress, or other states are not limited to aviation headsets, audio eyeglasses, military eyeglasses, or the configuration of the aviation headsets illustrated in FIGS. 1A-1B or audio eyeglasses illustrated in FIG. 2. Aspects cover any wearable consumer device having electrodes configured to collect electrical signals without the use of an external camera.

Aviation headsets are a type of wearable audio device that are used by pilots in both general aviation and commercial aviation. Such headsets can be connected to aircraft communication systems, for example to communicate with air-traffic control (ATC) or with other pilots. The headsets can also be used as a public addressing system, for example, for the pilots to speak with passengers on board the aircraft. The aircraft communication systems typically include an analog communication system such as an intercom. In some cases, such an intercom system can be configured to communicate over the very-high-frequency (VHF) bands (e.g., 18 MHz to 136.975 MHz) wherein each channel is separated from the adjacent ones by a band of pre-specified width (e.g., 8.33 kHz in Europe, 25 kHz elsewhere). An analog modulation technique such as amplitude modulation (AM) can be used for the communications, and the conversations may be performed in simplex mode. In some cases, for example, for trans-oceanic flights, other frequency bands such as high-frequency (HF) bands can be used for satellite communications. Aviation headsets may be used, for example, by pilots and air-traffic controllers to communicate with one another.

FIG. 1A illustrates an example of an aviation headset 100, according to aspects of the present disclosure. The headset 100 includes an ear-cup 105 on each side, which fits on, around, or over the ear of a subject. Each of the ear-cups 105 houses acoustic transducers or speakers. The headset 100 also includes an over-the-head bridge 110 for connecting the two ear-cups 105. In some implementations, a microphone 115 (e.g., a boom microphone) may be physically connected to one of the ear-cups 105. The headset 100 can be connected to the aircraft intercom system using the connecting cable 120, which may also include a control module 125 that includes one or more controls for the headset 100. The analog signals to and from the aircraft intercom system are transmitted through the wired connection provided by the connecting cable 120.

While the example in FIG. 1 illustrates an aviation headset that includes around-ear ear-cups, aviation headsets having other form-factors, including those having in-ear headphones or on-ear headphones, are also compatible with the technology described herein. In an example involving in-ear headphones, the over-the-head bridge may be omitted, and the boom microphone may be attached to the subject via the headset or via a separate structure. Also, the term headset, as used in this document, includes various types of acoustic devices that may be used for aviation purposes, including, for example, earphones and earbuds.

FIG. 1B illustrates an example of an aviation headset 150, according to aspects of the present disclosure. The headset 150 includes a headband having an arcuate section 155, a right end, and a left end. A right housing 160A and a left housing 160B are located at the right end and the left end, respectively, of the headband. The arcuate section 155 serves as an over-the-head bridge between the right housing 160A and the left housing 160B. A spring band 165 (e.g., spring steel) extends from the right housing 160A, through the arcuate section 155 and to the left housing 160B. The spring band 165 provides a clamping force to move the housings 160A, 160B toward each other (approximately along a horizontal plane through the wearer's head) while the headband is worn by a user. The right and left housings 160A, 160B can be moved a distance either up and toward or down and away from the arcuate section 155 to accommodate a smaller or larger head, respectively.

A right pad 170A is attached to housing 160A and a left pad 170B is attached to housing 160B. The pads 170A and 170B are used to comfortably secure the headset 150 to the head. As used herein, a "pad" means a compliant member that can compress and/or deform under an applied pressure and that is configured for contact with the head of a user in a manner that supports the headband. In aspects, each of the pad 170A and 170B includes a contoured surface 175A and 175B, respectively. The contoured surface substantially matches a contour of the head in a "contact region" where each of the pads 170A and 170B are adjacent to the head.

When the headset 150 is worn on the head, each pad 170A, 170B extends from its forward end above the ear to its back end, which is lower on the head and behind the ear. Thus, the pads 170A, 170B avoid applying pressure in front of the ear and in the temple region where user sensitivity is greater and discomfort would typically result.

A boom 180 extends from a rotatable base 185 near the bottom of one of the housings (e.g., as illustrated, the right housing 160A) and is used to position and support a microphone 190 attached at the other end.

A connector 196 for a communications cable extends from the bottom of the right housing 160A. The communications cable may have one or more conductors to conduct electrical signals such as a microphone signal and/or an audio signal. An earbud connector cable extends at one end from each housing 160A, 160B. The earbud connector cable 195B is illustrated extending from the left housing 160B in FIG. 1B. The opposite end of the connector cable is suitable for connecting to an earbud or other type of in-ear headphone.

FIG. 2 illustrates an example pair of audio eyeglasses 200. In an aspect, audio speakers are housed within the frame of the audio eyeglasses. In an example, electronics including the audio speaker are housed in the areas 202a and/or 202b. In non-illustrated examples, the audio eyeglasses include around-ear ear-cups, in-ear headphones, or on-ear headphones. In an aspect, audio eyeglasses 200 are in communication with a processor 210. Although illustrated as a separate block, processor 210 may be either internal or external to the audio eyeglasses 200. The processor 210 may, for example, be part of a portable user device with either a wired or wireless connection to the audio eyeglasses 200.

Figure 3:
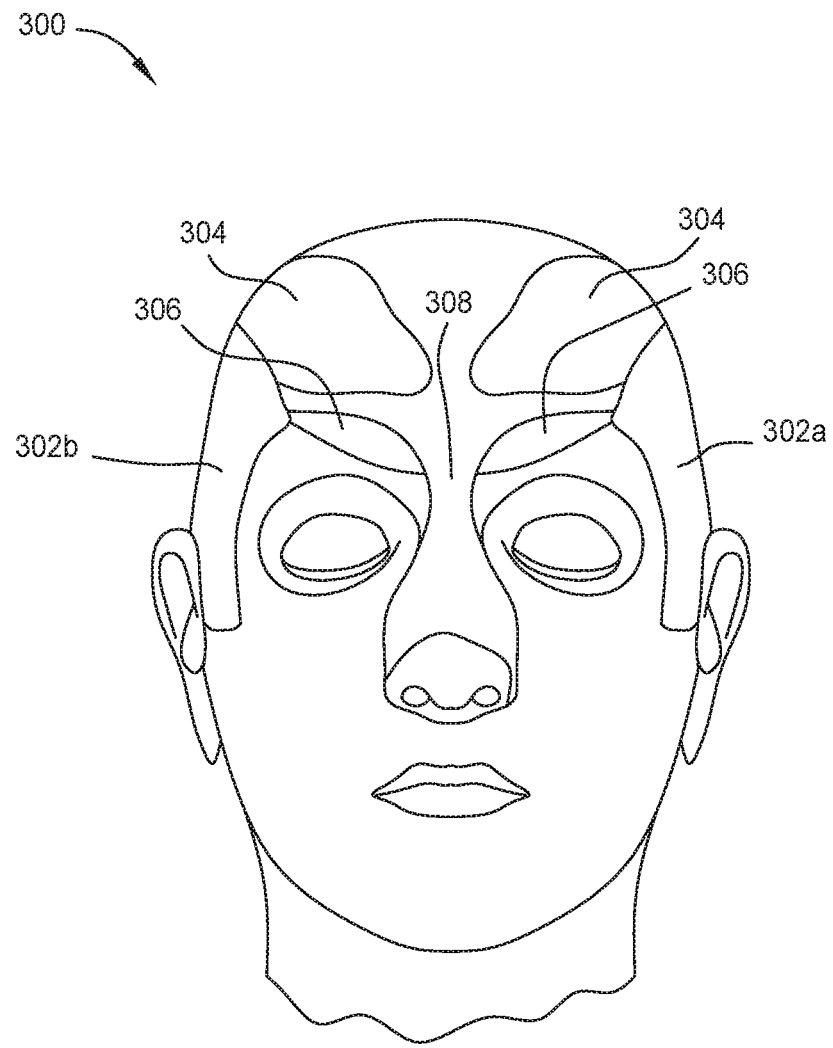
FIG. 3 illustrates muscles of an example human head.

As described herein, a wearable audio device including, but not limited to a headset (such as an aviation headsets 100 or 150) and audio eyeglasses (such as eyeglasses 200) include electrodes strategically placed on the device to collect electrical potential energy from the subject wearing the device. The electrical potential information is used to determine one or more of a level of fatigue, eye movement including eye blink duration and frequency of blinks, a level of attentiveness, a direction of gaze, HR, HRV, and a level of stress or anxiety. The intelligence for translating the raw data detected by the electrodes on the wearable audio device into determining one or more of a level of fatigue, eye movement, a level of attentiveness, a direction of gaze, HR, HRV, and a level of stress or anxiety resides in the wearable audio device, the user device, the cloud, or in a combination thereof. FIG. 3 illustrates muscles of an example human head 300. Electrical activity measured from regions of the human head provide information associated with the subject's eye blinking, eye movement, and heart rate activity. The left temporalis 302a, right temporalis 302b, occipitofrontalis 304, corrugator supercilii 306, and procerus 308 are referenced herein.

Figure 4:
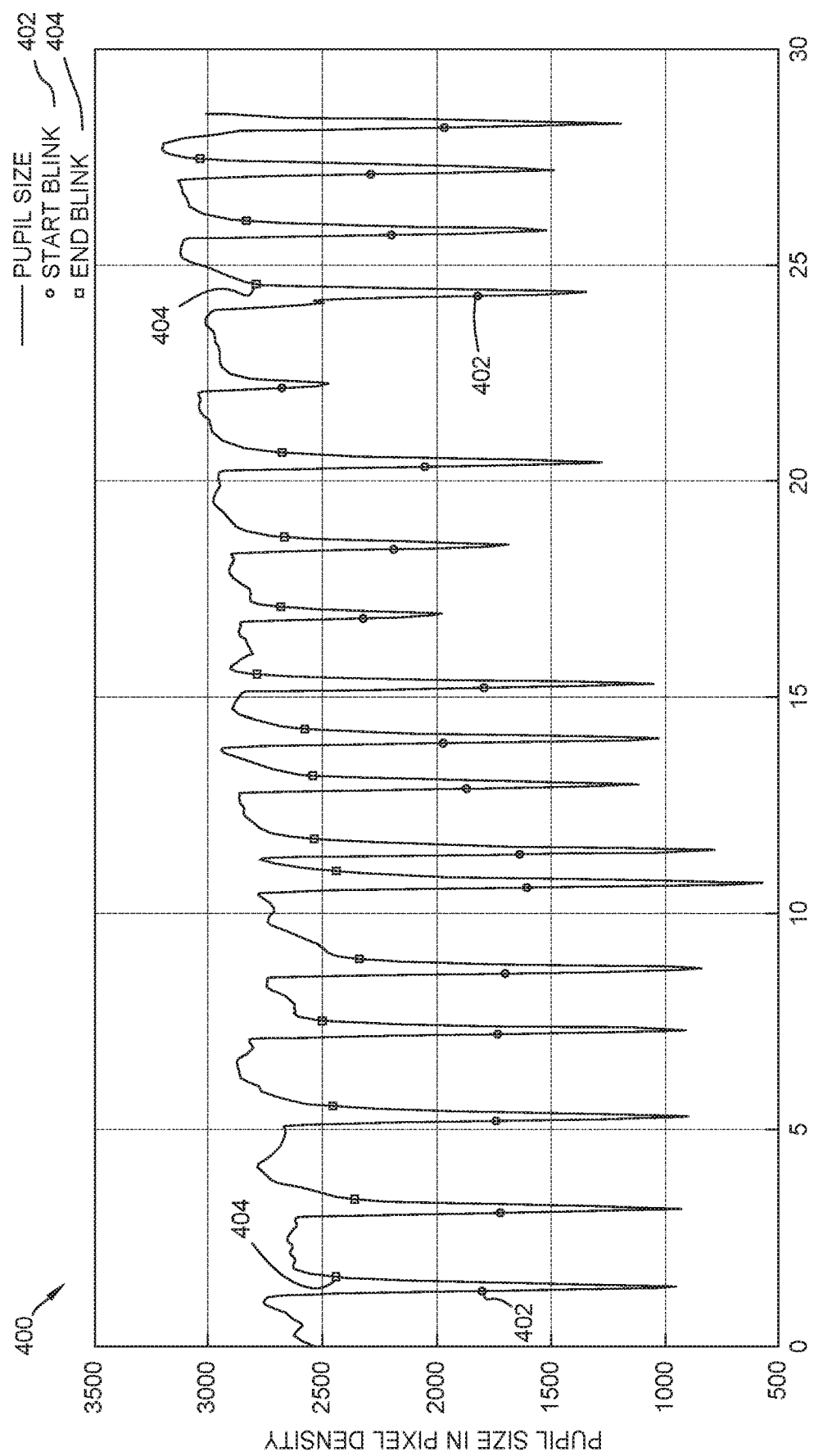
FIG. 4 illustrates a plot of pupil size as a function of frames measured using data from a video recording.
Figure 5:
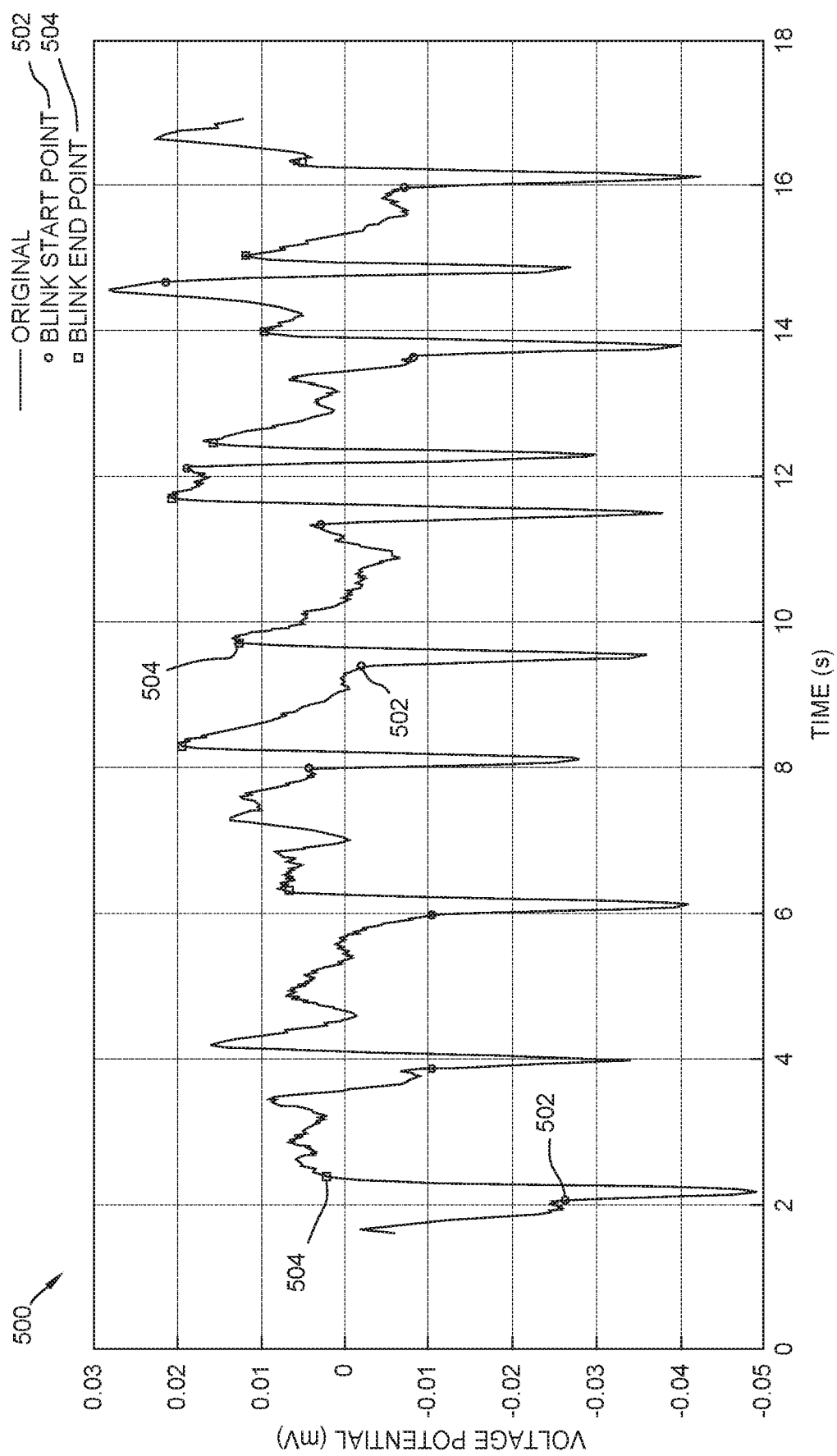
FIG. 5 illustrates a plot of the voltage potential between an electrode positioned over the temporalis region and an electrode positioned over the procerus region.
Figure 6:
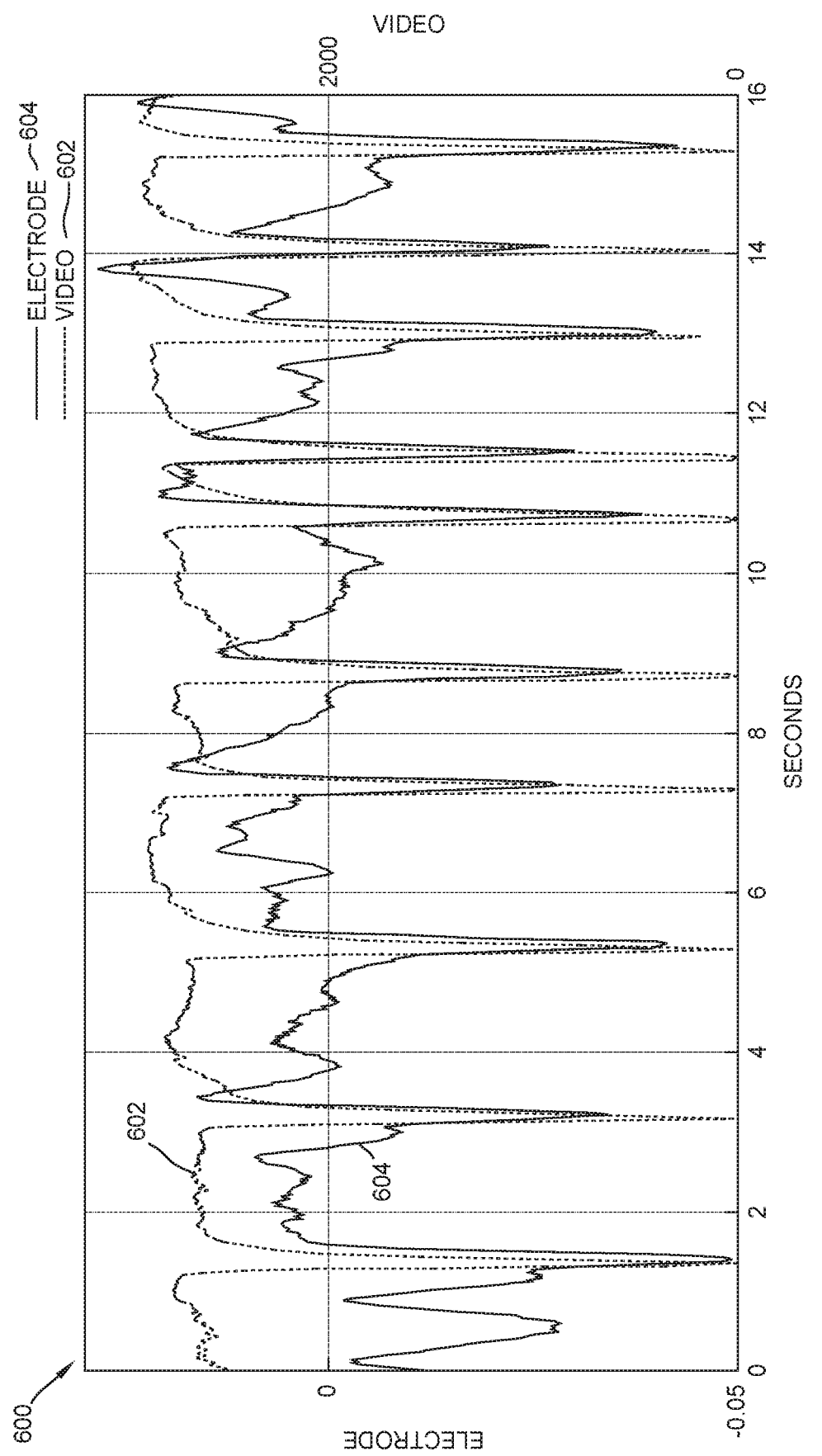
FIG. 6 illustrates time-adjusted, overlapping plots representing the video and voltage potential measurement data.

FIGS. 4-6 demonstrate that a subject's blink frequency and blink duration can be estimated using electrodes positioned on the subject's body. In this example, a dry electrode was positioned over each of the temporalis regions and the procerus region of the subject. While dry electrodes were used in this example, wet or semi-wet electrodes may be used to estimate a subject's blink frequency and blink duration. FIG. 4 shows a plot of pupil size measurements in pixel density on the y-axis as a function of frames on the x-axis as measured using data from a video recording. A threshold value of the slope of the plot was used to determine the start 402 and end 404 of the subject's blinks. FIG. 5 illustrates a plot of the voltage potential between the electrodes positioned over the temporalis region. A threshold value of the slope of the plot was used to determine the start 502 and end 504 of the subject's blink.

The start, end, and blink duration were recorded for each of the video recordings illustrated in FIG. 4 and the voltage potential measurements illustrated in FIG. 5. A blink start delta between the start time of a blink determined using the video recording and the start time of a blink determined using voltage potential measurements was calculated to correlate the blink start times determined using the video recording and the blink start times using voltage potential measurements. FIG. 6 illustrates time-adjusted, overlapping plots representing the video 602 and voltage potential measurement 604 data. FIG. 6 illustrates that each blink results in a large drop in the electrical potential measured by the electrodes. Therefore, a subject's blink frequency and blink duration can be estimated using electrical signals measured from the electrodes placed over the right and left temporalis regions and procerus region. Because signals collected from the temporalis region, in combination with the procerus region can be used to estimate a subject's blink duration and frequency, electrical signals measured from regions around other muscles near the eyes may also be used to estimate a subject's blink duration and frequency. In examples, electrodes measure electrical signals over or near the frontal belly of occipitofrontalis or corrugator supercilii to determine a blink duration and frequency.

In one aspect, electrical activity produced by skeletal muscles is used to determine when a subject blinks his or her eyes. In an example, an electrode is placed over each of the left temporalis region 302a, the right temporalis region 302b, and one of: the frontal belly of occipitofrontalis 304, corrugator supercilii 306, or procerus 308, and the electrodes are used to collect electromyogram (EMG) signals to determine when the subject blinks. The signals are used to determine a frequency of blinking and/or the duration of blinks.

A headset form factor, such as an aviation headsets 100 and 150, are well-suited to include an electrode over each of the left and right temporalis regions and an electrode over the frontal belly of occipitofrontalis. In an example, the three electrodes are positioned on the over-the-head bridge 110 in the headset 100. In an example, an electrode is positioned on each of the pads 170A and 170B of the headset 150 to collect signals from the left and right temporalis regions on the subject. In an aspect, an electrode is placed on the arcuate section 155 of headband over the frontal belly of occipitofrontalis 304.

In an example, an audio eyeglass form factor 200 includes an electrode over each of the left and right temporalis regions and an electrode over either the corrugator supercilii or procerus regions. Electrodes positioned over the left and right temporalis regions may be positioned in the regions 208a and 208b, respectively. The region 208a is on the left arm of the audio eyeglasses 200 and the region 208b is on right arm of the audio eyeglasses 200. An electrode positioned over the corrugator supercilii 306 may be positioned over one of the eyebrows in one of the regions 204a or 204b. An electrode positioned over the procerus 308 may be positioned on the bridge area 206 of the eyeglasses 200.

Figure 7:
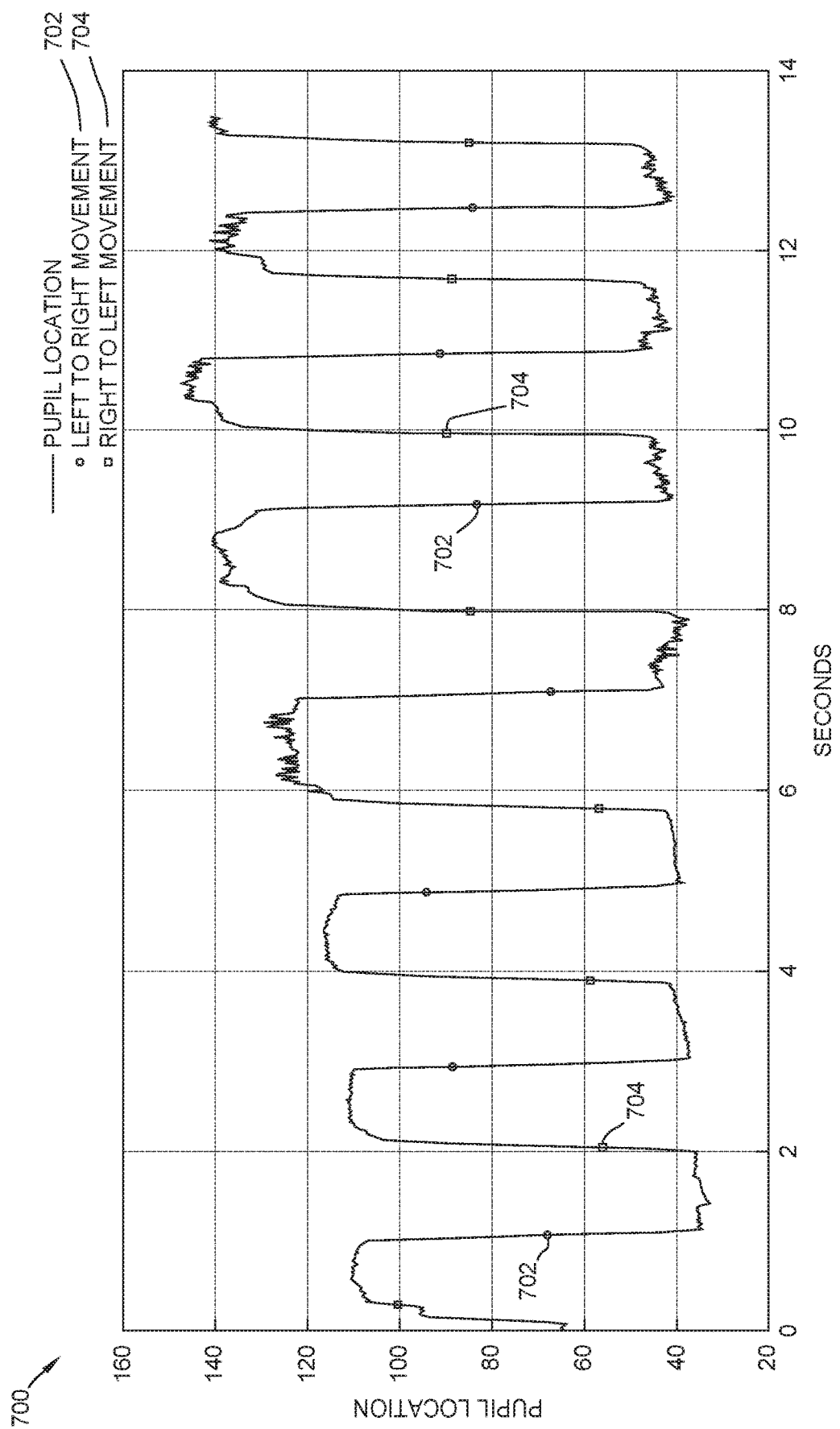
FIG. 7 illustrates a plot of pupil location as a function of frames.
Figure 8:
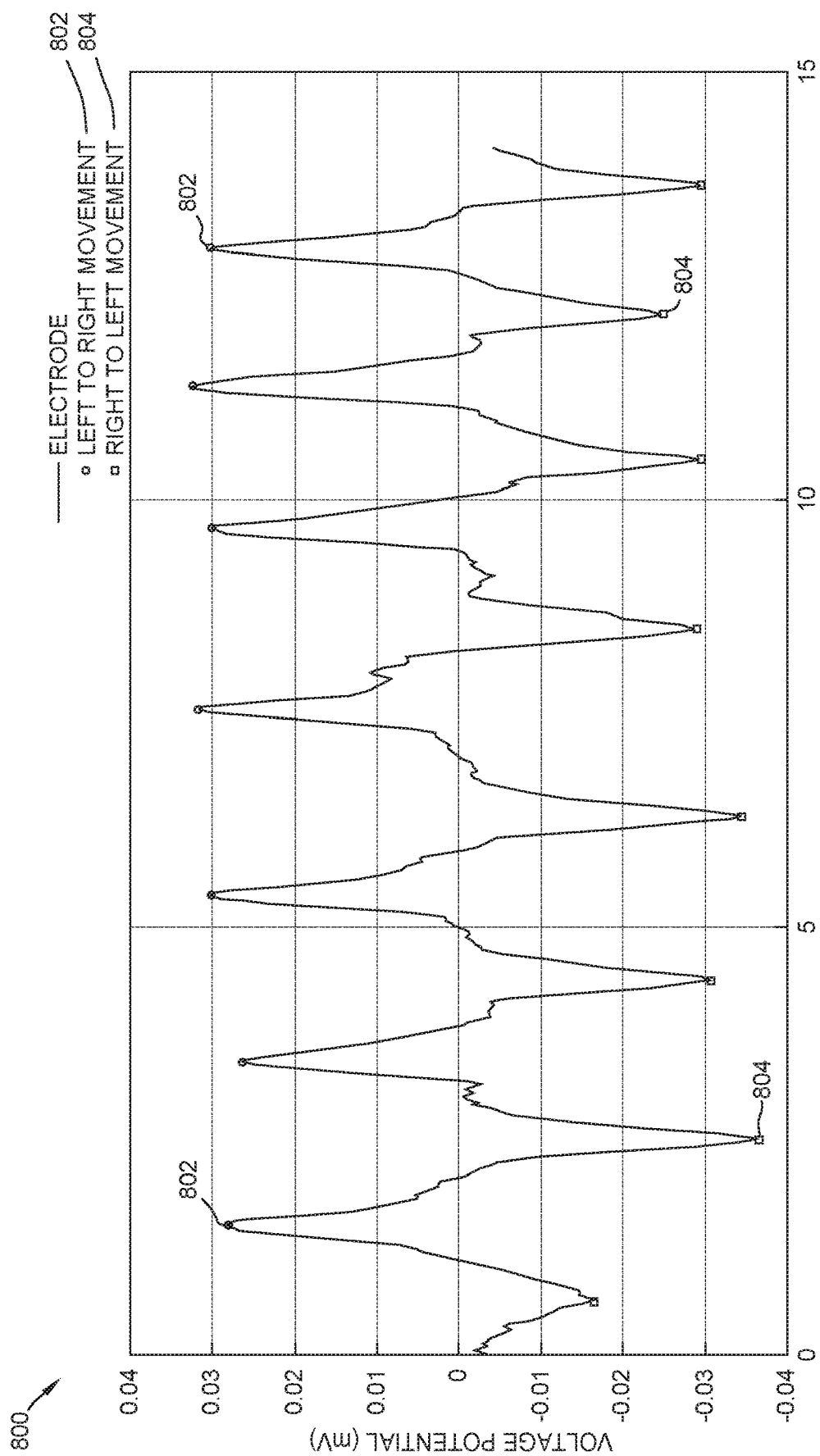
FIG. 8 illustrates a plot of the voltage potential between an electrode positioned over the left temporalis region and an electrode positioned over the right temporalis region.
Figure 9:
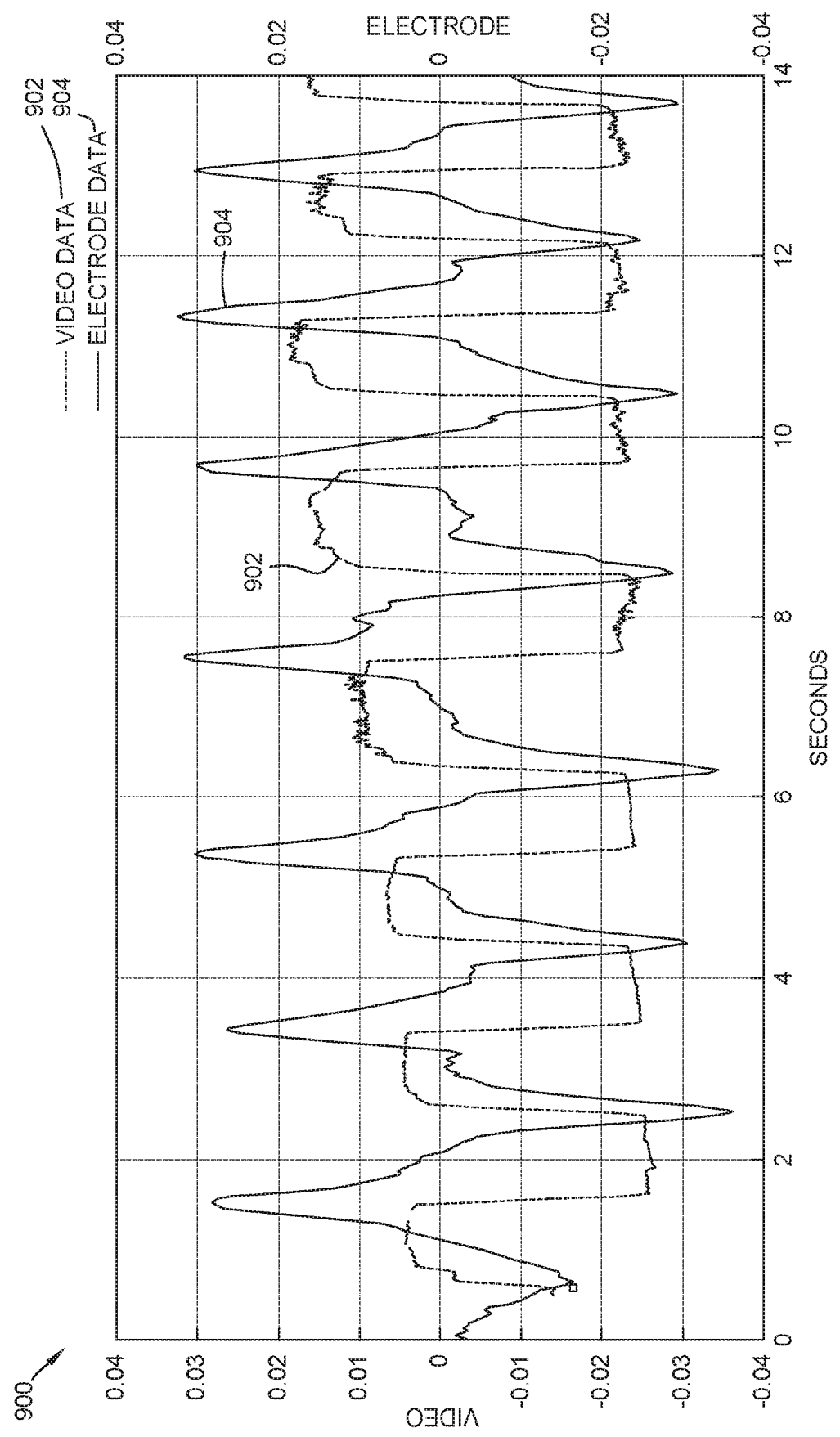
FIG. 9 illustrates time-adjusted, overlapping plots representing video data and voltage potential measurement data.

FIGS. 7-9 demonstrate that a subject's pupil movement can be estimated using electrodes positioned on the subject's body. Pupil movement refers to the subject's pupil moving from the left side of the subject's body to the right side of the subject's body or vice a versa. In this example, a dry electrode was positioned over each of the left and right temporalis regions of the subject and over the procerus region. FIG. 7 shows a plot of pupil location on the y-axis as a function of frames on the x-axis as measured using data from a video recording. In FIG. 7, values of 100 and greater on the y-axis indicate the subject is looking towards the left and values less than 50 indicate the subject is looking towards the right. The maximum positive slope of the plot was used to determine the right-to-left pupil movement and the maximum negative slope of the plot was used to determine the left-to-right pupil movement. The left-to-right movement is marked at 702 and the right-to-left movement is marked at 704. FIG. 8 illustrates a plot of the voltage potential between the electrodes positioned over the left and right temporalis regions. The maximum negative value was used to determine right-to-left pupil movement and the maximum positive value was used to determine the left-to-right pupil movement. The left-to-right pupil movement is marked at 802 and the right-to-left pupil movement is marked at 804. A delta time difference was calculated between a left-to-right movement as determined by the video recording and a corresponding left-to-right movement as determined by the voltage potential measurements. The voltage potential time data was adjusted based on the delta time difference. FIG. 9 illustrates time-adjusted, overlapping plots representing the video data 902 and the voltage potential measurement data 904. As seen in FIG. 9, the peaks and valleys of the video data 902 correlate with the peaks and valleys of the voltage potential measurement data 904, thereby demonstrating eye movement is represented by electrical potential activity.

In one aspect, electrodes placed over the left temporalis region 302a and right temporalis region 302b collect electrical signals called EOG signals. EOG signals provide information related to the subject's pupil movement, including left-to-right and right-to-left movement. In one example, an EOG signal is measured using an electrode placed over the left temporalis region 302a, an electrode placed over the right temporalis region 302b, and a third electrode. In an example, the third electrode is placed anywhere on the subject's head.

A headset form factor, such as an aviation headset 100, is well-suited to include an electrode over each of the left and right temporalis regions and a third electrode. In an example, the three electrodes are positioned on the over-the-head bridge 110. In another example, the electrodes measuring electrical activity from the left and right temporalis regions are positioned on the over-the-head bridge 110 and the third electrode is placed someplace else on the headset 100.

In an example, the aviation headset 150 includes an electrode over each of the left and right temporalis regions and a third electrode. An electrode is positioned on the right pad 170A to collect signals from the right temporalis region of the subject and another electrode is positioned on the left pad 170B to collect signals from the left temporalis region of the subject. One or more third (or reference) electrodes are placed any place on the headset 150.

In an example, an audio eyeglass form factor 200 includes an electrode over each of the left and right temporalis regions and a third electrode. Electrodes positioned over the left and right temporalis regions may be positioned in the regions 208a and 208b or anywhere on the left and right arms of the audio eyeglasses 200. A third electrode may be positioned any place on the eyeglasses 200.

The human head is a rich source for measuring voltage potential between two electrodes. In an example, a subject's HR or HRV is determined using the same form factor configured to determine a subject's level of fatigue and/or eye movement. Unlike determining a level of fatigue or eye movement, determining a HR or HRV may typically not require use of a camera. Estimating a subject's HR or HRV allows the wearable audio device to obtain additional information related the subject's level of stress or anxiety. In aspects, the subject's level of stress or anxiety is used in combination with the determined level of fatigue or eye movement to determine a more complete understanding of the subject's physiological condition.

In an example, electrodes placed over the left temporalis region 302a and right temporalis region 302b collect electrical signals called an ECG or EKG. An ECG signal provides information related to the subject's HR and HRV. HRV refers to the variation in the time interval between heartbeats. In one example, the ECG signal is measured using an electrode placed over the left temporalis region 302a and an electrode placed over the right temporalis region 302b.

A headset form factor, such as an aviation headset 100 and 150, is well-suited to include an electrode over each of the left and right temporalis regions. In an example, the electrodes are positioned on the over-the-head bridge 110 of the headset 100. In an example, the electrodes are and positioned on the pads 170A and 170B of the headset 150.

In an example, an audio eyeglass form factor 200 includes an electrode over each of the left and right temporalis regions. Electrodes positioned over the left and right temporalis regions may be positioned in the regions 208a and 208b, respectively. The region 208a is on the left arm of the audio eyeglasses 200 and the region 208b is on right arm of the audio eyeglasses 200.

As described in the preceding paragraphs and shown in FIGS. 1A, 1B, and 2, by leveraging the form factor of the headset or eyeglasses, electrodes collect information used to determine a state of a subject. In one aspect, a single headset includes one electrode positioned over the frontal belly of occipitofrontalis, one electrode on the headset positioned over the right temporalis region, and one electrode on the headset positioned over the left temporalis region. A processor, either internal or external to the headset, is configured to determine EMG based on signals collected from the electrodes. Based on the EMG, the processor is configured to determine a frequency and/or duration of eye blinking. Based on the frequency and/or duration of eye blinking, the processor is configured to determine a level of fatigue.

A level of fatigue can be absolute or relative. As a subject becomes more fatigued, his or her frequency of blinking and blink duration both increase. In an example, the processor may output an indication to alert the subject when one or both of the frequency of blinking and duration of blinks exceed a respective threshold value. In an example, the processor determines the frequency of blinking and blink duration for a configurable amount of time to determine if the frequency or blink duration exceed the threshold values.

In another example, the processor tracks historical information to determine a baseline blink frequency and duration. Using a machine-learning algorithm, the processor determines when the subject is fatigued based on the historical information specific to that subject. In this manner, a level of fatigue is personalized for each subject. According to aspects, a level of fatigue is determined, at least in part, based on the subject's environment, activities, or a configurable mode of operation of the wearable audio device. For example, using sensors or user-input received via an application on a user device, the wearable audio device may determine the subject is in an airplane, vehicle, or working.

In response, the wearable audio device is configured to operate in a first, heightened mode. In the heightened mode, the processor may decrease the threshold blink duration or threshold blink frequency for determining the subject is fatigued so that the wearable audio device errs on the side of, at times, overcautiously alerting the subject when he or she may be fatigued. The alert may be an acoustic or haptic output by one or more of the wearable audio device or the user device. Additionally or alternatively, the alert may include a report transmitted to a third party notifying the third party of the subject's determined state. In a non-heightened, normal mode, the threshold blink frequency and threshold blink duration increase in an effort to decrease the likelihood of the processor determining the subject is fatigued when he or she is not fatigued.

In an aspect, the processor is further configured to determine an EOG based on the signals collected from an electrode positioned on the right side of the subject's body and an electrode positioned on the left side of the subject's body. In an example, the electrodes are positioned over the right and left temporalis regions. The processor is configured to determine pupil movement of the subject based on the EOG, wherein the pupil movement comprises at least one of a pupil moving from left-to-right or the pupil moving from right-to-left. According to aspects, eye movement is used as a proxy to determine attentiveness. In certain environments, a subject's eyes, such as in an aviation, military, or automotive setting, are surrounded by several gauges. Accordingly, the subject's pupils should be moving in order to pay attention to his or her surroundings. If a subject's pupils are moving less than a threshold amount of times in a given time period, the subject may not be alert or attentive to his or her setting. A lack of attentiveness may indicated the subject is not situationally aware. Eye movement is also used to determine a direction of gaze or as a mechanism for giving user input to a wearable audio device.

Similar to blink duration and blink frequency, determining attentiveness based on eye movement may be absolute or relative. In an example, the processor may output an indication to alert the subject or a third-party when left-to-right or right-to-left eye movements fall below a threshold amount over a period of time.

In another example, the processor tracks historical information to determine a baseline of the subject's eye movement. Using a machine-learning algorithm, the processor determines when the subject is attentive and not attentive based on historical information specific to the subject. In this manner, alertness is personalized for each subject. According to aspects, alertness is determined, at least in part, based on the subject's environment, activities, or a configurable mode of operation of the wearable audio device. In the first heightened mode, the processor may decrease the threshold eye movement for determining the subject is not alert or not attentive so that the wearable audio device errs on the side of, at times, overcautiously alerting the subject when he or she may lack adequate situational awareness. In the non-heightened, normal mode, the threshold eye movement increases in an effort to decrease the likelihood the processor determines the subject is not alert when he or she is sufficiently alert for the given scenario.

According to aspects, the processor is further configured to determine an ECG or EKG based on the signal collected from the electrode positioned over the right temporalis region and the electrode positioned over the left temporalis region. The processor is configured to determine a HR or HRV based on the ECG or EKG. The processor is configured to determine a level of stress or anxiety of the subject based on the HR or HRV.

Similar to blink duration, blink frequency, and eye movement, determining a state of stress or anxiety may be absolute or relative. In an example, the processor may output an indication to alert the subject when his or her HR or HRV increases above a threshold amount.

In another example, the processor tracks historical information to determine a baseline HR and HRV of the subject. Using machine-learning algorithms, the processor determines when the subject is anxious or stressed based on historical information specific to the subject. According to aspects, stress and anxiety is determined, at least in part, based on the subject's environment, activities, or a configurable mode of operation of the wearable audio device. In the first, heightened mode, the processor may decrease the threshold HR or increase a threshold HRV for determining the subject is stressed or anxious so that the wearable audio device errs overcautiously alerting the subject when he or she may be stressed or anxious. In the non-heightened, normal mode, the processor adjust the thresholds in an effort to decrease the likelihood the processor determines the subject is stressed or anxious when he or she is sufficiently calm or relaxed.

In one aspect, a wearable audio device includes one electrode positioned on the bridge of audio eyeglasses over the procerus of a subject wearing the device, one electrode positioned over the right temporalis of the subject, and one electrode positioned over the left temporalis of the subject. In one example, the electrode positioned over the right temporalis is disposed on the right arm of the audio eyeglasses and the electrode positioned over the left temporalis is disposed on the left arm of the audio eyeglasses.

A processor, either internal or external to the wearable audio device, is configured to determine EMG based on signals collected from the electrodes. Based on the EMG, the processor is configured to determine a frequency and/or duration of eye blinking. Based on the frequency and/or duration of eye blinking, the processor is configured to determine a level of fatigue.

In an aspect, an EOG is determined based on the signals collected from the electrode positioned over the right temporalis and the electrode positioned over the left temporalis. Pupil movement is determined based on the EOG. In aspects, a level of attentiveness or direction of gaze is determined based on the pupil movement.

In an aspect, ECG/EKG is determined based on the signals collected from the electrode positioned over the right temporalis and the electrode positioned over the left temporalis. HR or HRV is determined based on the ECG/EKG. The HR and/or HRV may indicate level of stress or anxiety. The methods for determining a level of fatigue, eye movement activity, level of alertness, HR, HRV, and level of stress and anxiety are similar to those described above.

In another example, audio eye glasses include one electrode positioned over the corrugator supercilii of a subject wearing the audio eyeglasses, one electrode on the audio eyeglasses positioned over the right temporalis of the subject, and one electrode on the audio eyeglasses positioned over the left temporalis of the subject. A processor, either internal or external to the eye glasses is configured to determine an EMG based on signals collected from the electrode positioned over the corrugator supercilii, the electrode positioned over the right temporalis, and the electrode positioned over the left temporalis. The processor is configured to determine a frequency and/or duration of eye blinking associated with the subject based on the EMG, and determine a level of fatigue of the subject based on the frequency and/or duration of eye blinking.

In aspects, the processor is further configured to determine an EOG based on the signals collected from the electrode positioned over the right temporalis and the electrode positioned over the left temporalis. The processor is further configured to determine pupil movement based on the EOG, and determine a level of attentiveness or direction of gaze of the subject based on the pupil movement In aspects, the processor is further configured to determine an ECG/EKG based on the signals collected from the electrode positioned over the right and left temporalis regions. A HR or HRV is determined based on the ECG/EKG. A level of stress or anxiety is determined based on the ECG/EKG. The methods for determining a level of fatigue, eye movement activity, level of alertness, HR, HRV, and level of stress and anxiety are similar to those described above.

In addition to using electrodes positioned on the wearable audio device to collect information used to determine a state of the subject, the electrodes are also used to enhance a user's experience with the wearable audio device. AR headsets or AR eyeglasses are used to create an immersive user experience that shuts out the physical world or enhances a user experience based on a location of the user. Information collected using the electrodes positioned as described herein help to create a more customized, immersive user experience.

A VR headset is a device that provides a simulated visual environment through physical display optic lenses, allowing the user to see both a digital display and the world through the display. An AR headset is a device that provides a simulated audio environment, allowing the user to hear digital audio, possibly layered on to the physical world around them, to augment his or her experience.

In an example, audio augmented reality or audio AR (e.g., Bose® AR) adds an audible layer of information and experiences based on what a user is looking at to enhance the user's audio experience. This audible layer of information is generally delivered to the user via some kind of a wearable audio device. Various sensors (e.g., one or more of an accelerometer, gyroscope, and magnetometer) are used to track motion of the user to determine a direction in which a user is looking. Further, GPS is used to track a location of the subject. The motion tracking and location information is used by an audio AR platform to aggregate real-time content relevant to what the user is looking at, which is streamed to the user's ears instantly.

In an example, pupil location determined using an EOG signal collected from electrodes positioned over the left and right temporalis regions of a subject wearing an AR wearable audio device are used by AR applications to enhance a subject's AR experience. For example, an AR headset or AR eyeglasses use GPS to track a physical location of the subject. Based on the determined pupil location, the AR device may determine where the subject is looking. Based on this the subject's physical location and pupil location, the AR device alters the audio output delivered to the subject.

A few examples of integrating a determined pupil location to enhance an AR experience are described. The example uses are illustrative of methods by which the subject's AR experience is augmented based on EOG feedback.

In one example, the subject is standing in front of a historical landmark and the EOG indicates the subject is not looking at the landmark. Instead, the subject is looking at his or her user device. The AR device may stop delivering informative audio content associated with the landmark because the subject does not appear to be interested in the landmark. If the subject's pupil location shifts towards the landmark, the AR device may begin delivering audible information associated with the landmark.

In another example, the AR device may determine the direction in which the subject is traveling. Based on the subject's physical path, the AR device alters the audio output delivered to the subject. In an example, the subject is using a map or navigation application (running on a device in communication with the wearable audio device). The map application determines the subject's physical location and path the subject has taken. The subject's pupil location is determined using an EOG signal collected using electrodes on the wearable audio device. The subject's pupil location, the subject's physical location, and the subject's physical path are used to determine if the subject is navigating towards specific point of interest. When the subject is not looking towards the point of interest, the AR device is configured to alter an AR output to redirect the subject towards the point of interest. In another example, AR device stops outputting an audio output associated with the point of interest until the subject is determined to be looking in the direction of the point of interest.

In another example, the subject is playing an AR game. When the subject's EOG indicates the subject is looking at a visual interface displaying the AR game, the AR headset or AR eyeglasses enhance the subject's AR experience by outputting content relevant to AR game. When the subject's EOG indicates the subject is not looking at the visual interface, the subject may not be engaged in the AR game. Accordingly, the wearable audio device may refrain from outputting audio content relevant to the AR game, limit the audio output relevant to the AR game, or output relevant audio content at a lower sound pressure level as compared to when the subject is looking at the visual interface.

According to aspects, pupil movement determined using the EOG signal is used to control the wearable audio device. In an example, a pattern of left-to-right and right-to-left pupil movement is associated with an action to be performed by the wearable audio device. The subject moves his or her pupils in accordance with a pattern to trigger the wearable audio device to take a configured action. Examples of actions include increasing or decreasing a volume of the audio output, skipping a song, turning a feature on or off, accepting a phone call using the wearable audio device, adjusting an ANR level, altering a mask output by the device, or activating a voice personal assistant.

Aspects provide systems for determining a state of a user including, but not limited to a state of fatigue, alertness, or anxiety using electrodes positioned on a wearable audio device. Advantageously, subjects may use wearable audio devices for work or pleasure. Strategically positioning electrodes on the wearable audio devices to collect EOG, EMG, and/or ECG signals helps to determine several states of a user in (near) real-time in a non-invasive manner. Any combination of the determined states may be feedback to the wearable audio device or output to the subject or third party.

In the preceding, reference is made to aspects presented in this disclosure. However, the scope of the present disclosure is not limited to specific described aspects. Aspects of the present disclosure may take the form of an entirely hardware embodiment, an entirely software embodiment (including firmware, resident software, micro-code, etc.) or an embodiment combining software and hardware aspects that may all generally be referred to herein as a "component," "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of a computer readable storage medium include: an electrical connection having one or more wires, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the current context, a computer readable storage medium may be any tangible medium that can contain, or store a program.

The invention claimed is:

1. A system comprising:
   a first electrode on a wearable audio device positioned on a first side of the wearable audio device;
   a second electrode on the wearable audio device positioned on a second side of the wearable audio device; and
   a third electrode on the wearable audio device, wherein the third electrode is configured to be positioned over one of the: frontal belly of occipitofrontalis of the subject, or corrugator supercilii of the subject; and
   a processor in communication with the wearable audio device configured to:
   determine an electromyogram based on signals collected from the first, second, and third electrodes;
   determine a frequency of eye blinking associated with a subject wearing the wearable audio device based on the electromyogram;
   determine a duration of eye blinking associated with the subject based on the electromyogram; and
   determine a level of fatigue of the subject based on the frequency and the duration of eye blinking.

2. The system of claim 1, wherein the processor is further configured to:
   determine an electrooculogram based on the signals collected from the first, second, and third electrodes;
   determine pupil movement of the subject based on the electrooculogram, wherein the pupil movement comprises at least one of a pupil moving from left to right or the pupil moving from right to left; and
   determine a level of attentiveness of the subject based on the pupil movement.

3. The system of claim 2, wherein the processor is further configured to:
   determine a direction of gaze of the subject based on the pupil movement.

4. The system of claim 1, wherein:
   the first electrode is configured to be positioned over the right temporalis of the subject; and
   the second electrode is configured to be positioned over the left temporalis of the subject.

5. The system of claim 1, wherein the wearable audio device comprises audio eyeglasses.

6. The system of claim 1, wherein the processor is external to the wearable audio device.

7. A system comprising:
a first electrode on a wearable audio device positioned on a first side of the wearable audio device;
a second electrode on the wearable audio device positioned on a second side of the wearable audio device; and
a third electrode on the wearable audio device, wherein the third electrode is configured to be positioned over one of the: frontal belly of occipitofrontalis of the subject, or corrugator supercilii of the subject; and
a processor in communication with the wearable audio device configured to:
determine at least one of: an electromyogram, an electrooculogram, and an electrocardiogram based on signals collected from the first, second, and third electrodes;
determine a frequency of eye blinking associated with a subject wearing the wearable audio device based on the electromyogram;
determine a duration of eye blinking associated with the subject based on the electromyogram; and
determine a level of fatigue of the subject based on the frequency of eye blinking.

8. The system of claim 7, wherein the processor is further configured to:
determine pupil movement of the subject based on the electrooculogram, wherein the pupil movement comprises at least one of a pupil moving from left to right or the pupil moving from right to left; and
determine a level of attentiveness of the subject based on the pupil movement.

9. The system of claim 8, wherein the processor is further configured to:
control the wearable audio device based on the pupil movement.

10. The system of claim 7, wherein the processor is further configured to:
determine a location of at least one pupil based on the signals collected from the first, second, and third electrodes; and
enhance an augmented reality output by the wearable audio device based, at least in part, on the location of the at least one pupil.

11. The system of claim 7, wherein:
the first electrode is configured to be positioned over the right temporalis of the subject;
the second electrode is configured to be positioned over the left temporalis of the subject; and
the third electrode is configured to be positioned over one of: the corrugator supercilii of the subject or the procerus of the subject.

* * * * *